(12) United States Patent
Brown et al.

(10) Patent No.: US 9,724,148 B1
(45) Date of Patent: Aug. 8, 2017

(54) SURGICAL SYRINGE DEVICES AND METHODS OF USE

(71) Applicants: Kevin Brown, Greenville, NC (US); Gregory Bauer, Goldsboro, NC (US)

(72) Inventors: Kevin Brown, Greenville, NC (US); Gregory Bauer, Goldsboro, NC (US)

( * ) Notice: Subject to any disclaimer, the term of this patent is extended or adjusted under 35 U.S.C. 154(b) by 466 days.

(21) Appl. No.: 13/959,261

(22) Filed: Aug. 5, 2013

Related U.S. Application Data

(60) Provisional application No. 61/680,050, filed on Aug. 6, 2012.

(51) Int. Cl.
*A61B 17/88* (2006.01)

(52) U.S. Cl.
CPC .................. *A61B 17/8811* (2013.01)

(58) Field of Classification Search
CPC A61B 17/8811; A61B 17/8808; A61F 2/4081
See application file for complete search history.

(56) References Cited

U.S. PATENT DOCUMENTS

| | | | |
|---|---|---|---|
| 3,606,094 A * | 9/1971 | Mills .................... | A61C 9/0026 222/145.6 |
| 4,472,141 A | 9/1984 | Dragan | |
| 4,646,752 A | 3/1987 | Swann et al. | |
| 5,286,257 A | 2/1994 | Fischer | |
| 5,346,495 A * | 9/1994 | Vargas, III ......... | A61B 17/8808 604/272 |
| 5,643,206 A | 7/1997 | Fischer | |
| 5,697,903 A | 12/1997 | Fischer | |
| 5,741,265 A * | 4/1998 | Chan .................. | A61B 17/8808 606/92 |
| 5,759,178 A | 6/1998 | Wells | |
| 5,938,439 A * | 8/1999 | Mertins .................. | A61C 5/066 433/90 |
| 6,309,372 B1 | 10/2001 | Fischer et al. | |
| 6,458,136 B1 * | 10/2002 | Allard ................ | A61B 17/1684 606/92 |
| 2002/0058946 A1 * | 5/2002 | Gross ................. | A61B 17/3421 606/93 |
| 2011/0034828 A1 | 2/2011 | Holmin et al. | |
| 2011/0035013 A1 * | 2/2011 | Winslow ............... | A61F 2/4003 623/19.13 |

FOREIGN PATENT DOCUMENTS

| | | |
|---|---|---|
| EP | 1 304 086 B1 | 3/2006 |
| KR | 20010081195 A | 8/2001 |

OTHER PUBLICATIONS

Toomey syringe. Jun. 12, 2013. Obtained at http://www.penncare.net/shop/p-72-disposable-toomey-syringe-dv-3846.aspx. Penn Care, Inc., Niles, OH.

* cited by examiner

*Primary Examiner* — Samuel Hanna
(74) *Attorney, Agent, or Firm* — Coats & Bennett, PLLC

(57) ABSTRACT

Devices and methods for inserting bone cement into a patient during a surgical procedure. The methods may include inserting a tip of a nozzle at the desired location in the patient, such as an opening formed in a bone. An enlarged radial member may be positioned against the bone and covers the opening. Cement is moved through the nozzle and into the opening. The member may prevent escape of the cement from the opening. The nozzle may also be configured to facilitate insertion of the cement at the desired location within the patient.

13 Claims, 12 Drawing Sheets

SURGICAL SYRINGE DEVICES AND METHODS OF USE

RELATED APPLICATION

The present application claims priority to U.S. Application No. 61/680,050 filed on Aug. 6, 2012 entitled Surgical Syringe Devices and Methods of Use, which is hereby incorporated by reference in its entirety.

BACKGROUND

The present application is directed to devices and methods for inserting surgical cement into a patient during a surgical procedure and, more particularly, to insertion of the surgical cement during a surgical procedure on a patient's shoulder.

Various surgical procedures use bone cement. Examples include procedures with various implants, such as hip joints, knee joints, and shoulder joints. The bone cement anchors the components to the bone and is positioned in the space between the implant and the bone to fill the intermediate gap. The bone cement may also provide for some elasticity for the implant.

An issue faced by surgical personnel during these procedures is inserting the cement at the proper location within the patient. Often times the surgical window used during the procedure is relatively small which makes it difficult for insertion of the cement. Further, the patient's anatomy often makes it difficult to insert the cement in the desired location. The shoulder is a particularly difficult location to work in during a procedure. The anatomy provides for difficulty in accurately positioning an insertion device to deliver the cement at the desired location.

SUMMARY

The present application is directed to methods and devices for inserting bone cement into a patient during a surgical procedure.

One embodiment is directed to a method of inserting bone cement and includes inserting a leading tip of a nozzle into an opening formed in a face of a glenoid cavity in the patient. The method includes moving the bone cement through an interior of the nozzle and through the leading tip and into the opening in the glenoid cavity. The method also includes stopping the flow of the cement through the leading tip and removing the leading tip from the opening.

The various aspects of the various embodiments may be used alone or in any combination, as is desired.

DETAILED DESCRIPTION

Figure 1:
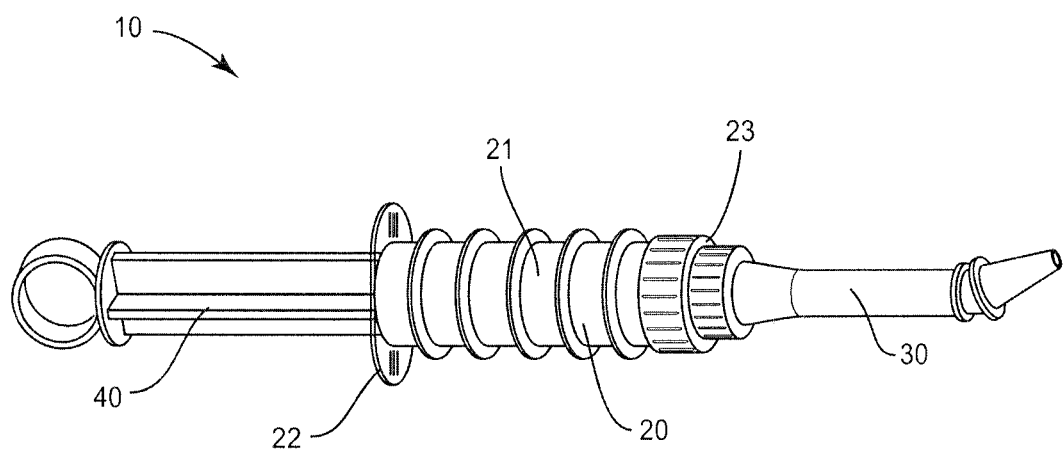
FIG. 1 is a perspective view of a device.

The present application is directed to devices and methods for delivering surgical cement into a patient during a surgical procedure. FIG. 1 illustrates one embodiment of the device 10 that generally includes a body 20, a nozzle 30, and a plunger 40. The device 10 is configured to hold the cement within the body 20 during insertion and positioning within the patient. The nozzle 30 may include an angled configuration to facilitate positioning within the patient. The plunger 40 is configured to move relative to the body 20 to force the cement from the body 20 and through the nozzle 30 for delivery into the patient.

Figure 2:
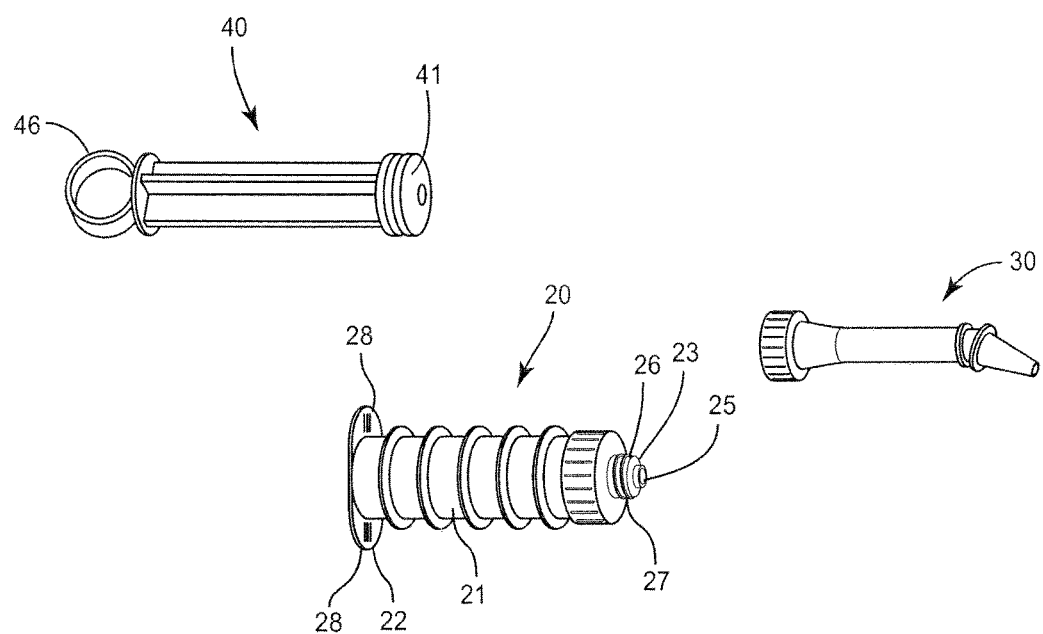
FIG. 2 is an exploded perspective view of a device.
Figure 3:
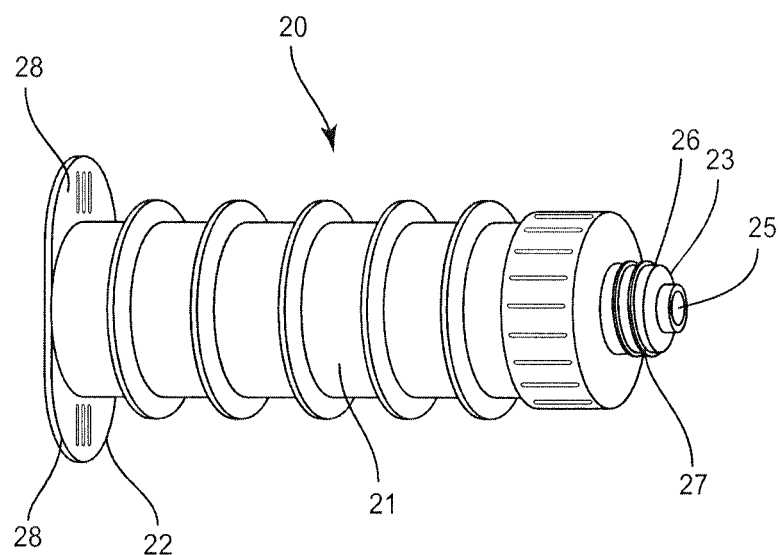
FIG. 3 is a perspective view of a body.

The device 10 may be constructed from separate components that are removably connected together. FIG. 2 illustrates the device 10 constructed from three separate components 20, 30, 40. Each of the components can be connected/unconnected as necessary. Other embodiments may include the device 10 constructed as a single component, two components, or more than three components.

The body 20 is configured to hold the cement prior to delivery to the patient. The body 20 includes an interior receptacle 21 to contain the cement. The interior receptacle 21 may include a variety of cross-sectional shapes, with one embodiment including a circular shape. The body 20 also includes a first end 22 and an opposing second end 23. The first end 22 includes an enlarged opening 24 that extends into the receptacle 21. Projections 28 may extend outward from the body 20 at the first end 22 to facilitate grasping of the body 20 and movement of the plunger 40 relative to the body 20.

The second end 23 includes a mount 26 to receive the nozzle 30. The mount 26 may include various structures, such as threads 27, to engage with the nozzle 30. An opening 24 extends from a bottom of the receptacle 21 through the interior of the mount 26. The opening 24 terminates at an outlet 25 at the second end 23. The cement moves through the opening 24 and into the patient through the outlet 25. In one embodiment, the opening 24 includes a smaller cross-section than the receptacle 21.

Figure 4:
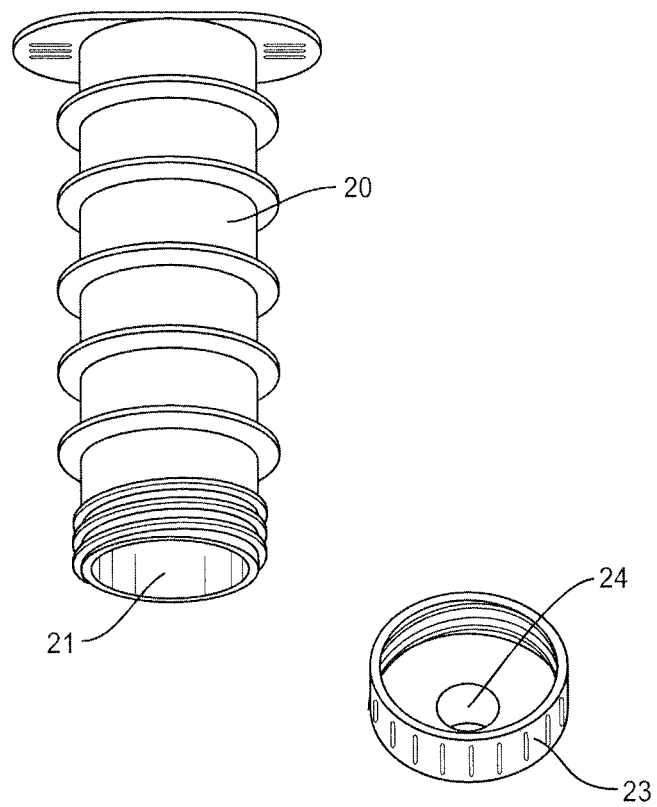
FIG. 4 is a perspective view of a body with a removable second end.

In one embodiment as illustrated in FIG. 4, the second end 23 is removable from the remainder of the body 20. The removable second end 23 and the body 20 may each include threads to engage together.

The nozzle 30 extends outward from the second end 23 of the body 20. The nozzle 30 includes an elongated shape with a first end 31 that faces towards the body 20, and an opposing second end 32. The length of the nozzle 30 measured between the ends 31, 32 may vary depending upon the application.

Figure 6:
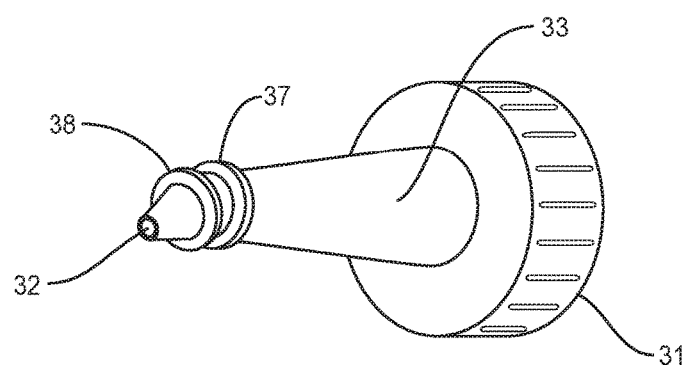
FIG. 6 is a perspective view into an end of the nozzle.

The nozzle 30 is hollow with an interior opening 33 that extends the length. The opening 33 is a conduit for the cement to flow from the receptacle 21 and through the nozzle 30. As illustrated in FIG. 6, the first end 31 may be threaded to removably attach to the second end 23 of the body 20.

Figure 5:
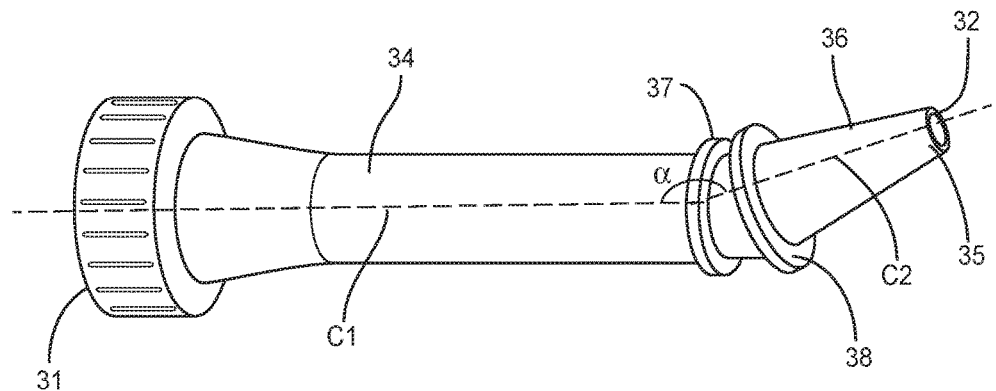
FIG. 5 is a perspective view of a nozzle.

In one embodiment as illustrated in FIG. 5, the nozzle 30 includes a first section 34 at the first end 31, and a second section 35 at the second end 32. The sections 34, 35 are oriented at an angle to facilitate positioning the second end 32 into the desired positions within the patient. As illustrated in FIG. 5, the centerline C1 of the first section 34 forms an angle α with the centerline C2 of the second section 35. The angle α may vary depending upon the application, with the angle α ranging from between about 130 degrees to about 160 degrees. In one specific embodiment, the angle is about 160 degrees.

Figure 7:
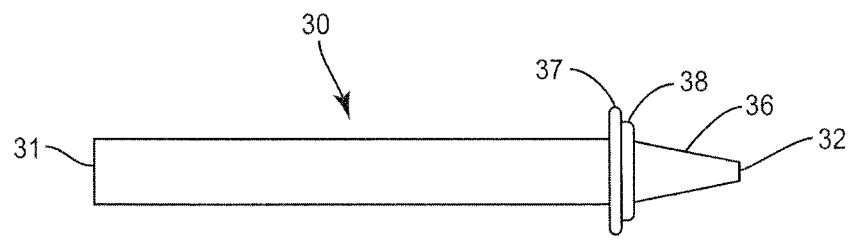
FIG. 7 is a side view of a section of a nozzle.

In another embodiment, the nozzle 30 is substantially straight throughout the length (i.e., there is no angle α formed between first and second sections). One embodiment is illustrated in FIG. 7.

Figure 8:
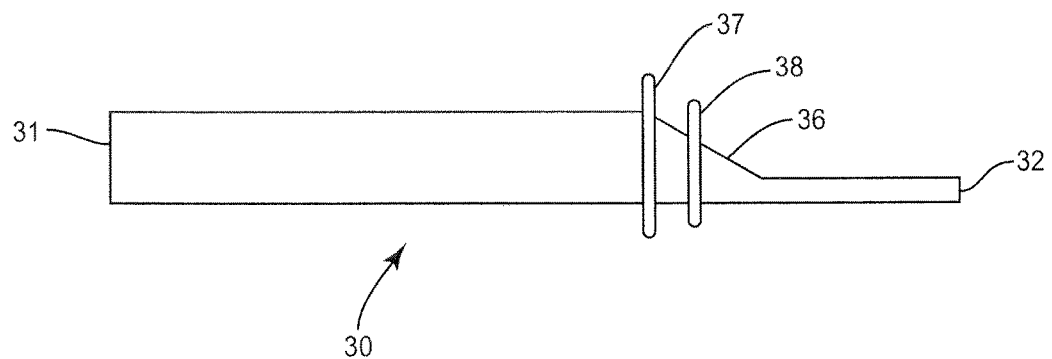
FIG. 8 is a side view of a section of a nozzle.
Figure 18:
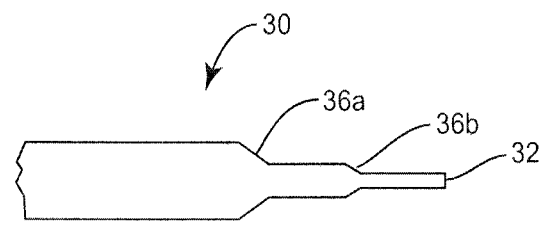
FIG. 18 is a partial side view of a nozzle.

The second end 32 of the nozzle 30 may include a tapered section 36 that reduces in size towards the second end 32. The tapered section 36 may be positioned at the second end 32 as illustrated in FIGS. 5 and 6. Alternatively, the tapered section 36 may be positioned inward from the second end 32 as illustrated in FIGS. 8 and 18. Further, the nozzle 30 may include a single tapered section 36, or multiple tapered sections as illustrated in FIG. 18 with a first tapered section 36a and a second tapered section 36b. In embodiment with multiple tapered sections 36, the sections may include the same or different shapes.

The tapered section 36 may be centered about the centerline of the nozzle 30. Other embodiments may include an offset tapered section 36. FIG. 8 illustrates an embodiment with an offset tapered section 36 that extends outward along a limited radial portion of the nozzle 30.

In one embodiment, the nozzle 30 does not include a tapered section 36.

The nozzle 30 may also include a positioning flange 37. The flange 37 extends radially outward beyond the remainder of the nozzle 30. In one embodiment, the flange 37 acts as a stop to control an extent of insertion of the nozzle 30 into an opening in the patient as will be explained in more detail below.

Figure 9:
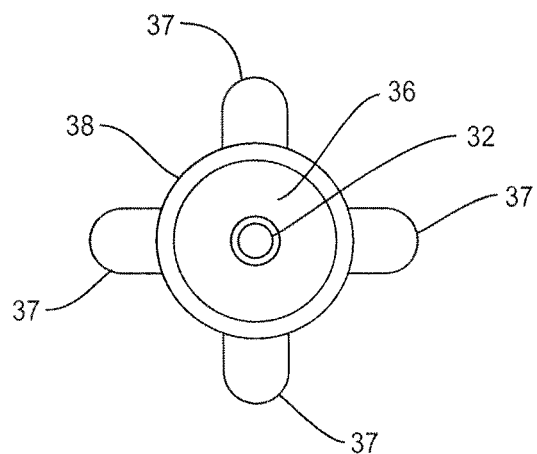
FIG. 9 is an end view of a nozzle.

The flange 37 may extend outward around the entire radial extent of the nozzle 30 as illustrated in FIGS. 5 and 6. Alternatively as illustrated in FIG. 9, the flange 37 may be formed by multiple sections that extend radially outward from limited portions of the nozzle 30.

In one embodiment, the flange 37 is positioned at the inner end of the tapered section 36 as illustrated in FIG. 5.

The nozzle 30 may also include a bumper 38 positioned in proximity of the second end 32. The bumper 38 is a flexible, resilient member. The bumper 38 may be constructed from various materials, including but not limited to a foam material.

Figure 10:
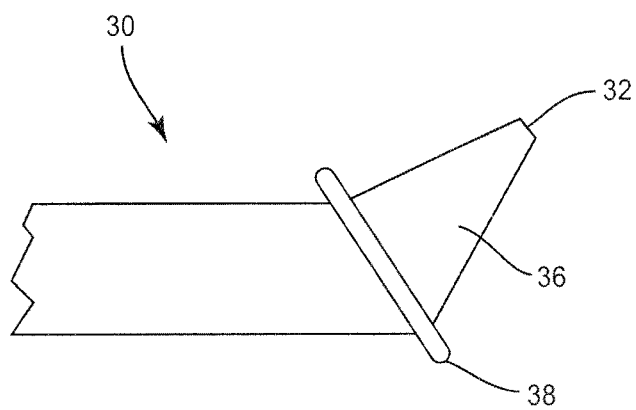
FIG. 10 is a partial side view of a nozzle.

FIG. 10 illustrates a bumper 38 attached to the nozzle 30 at the tapered section 36. The bumper 38 extends around the nozzle 30 and includes an inner side that abuts against the nozzle 30.

The bumper 38 may be attached to the nozzle 30 in a variety of manners. One embodiment includes the bumper 38 affixed by an adhesive. Another embodiment includes attachment via one or more mechanical fasteners. Another embodiment includes the bumper 38 be constructed from a resilient material with an interior opening being smaller than the nozzle 30 such that the resiliency of the material maintains the attachment.

In one embodiment, the bumper 38 is positioned against the outer side of the flange 37. In use, the bumper 38 abuts against the flange 37 on one side and bone within the patient on the opposing second side to prevent cement that has been delivered from the second end 32 to leak into the patient.

In one embodiment, the bumper 38 has an annular shape that contacts against the patient to prevent leaking. In one embodiment, the bumper 38 is positioned between the flange 37 and the second end 32.

Figure 11:
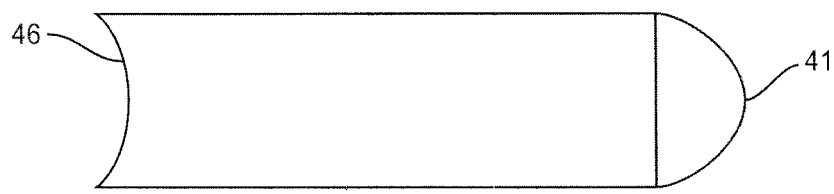
FIG. 11 is a side view of a plunger.

Returning to the overall device 10, the plunger 40 is sized to fit within the receptacle of the body 20 to force the cement into and through the nozzle 30. The plunger 40 includes an inner end 41 that is inserted into the receptacle 21, and an outer end 46 that is gripped/contacted by the surgeon. In one embodiment as illustrated in FIG. 11, the outer end 46 includes a concave shape. The outer end 46 may also include a coating to facilitate the gripping/contacting. In one embodiment, the coating is a rubber.

The device 10 may be used for a variety of different surgical procedures, examples include but are not limited to a shoulder replacement surgery.

Figure 12:
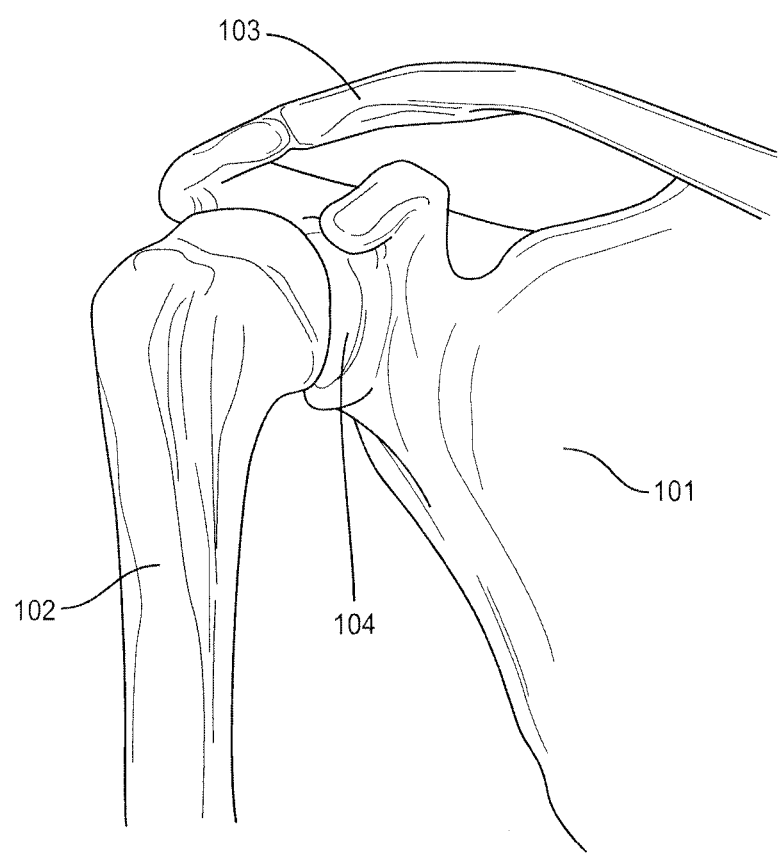
FIG. 12 is a schematic view of a humerus, scapula, and clavicle.

One specific use of the devices 10 is during shoulder replacement surgery. FIG. 12 illustrates the anatomy of the shoulder that includes the scapula 101 that includes the glenoid cavity 104, the humerus 102, and the clavicle 103. The surgical procedure includes treatment of the humerus 102 and scapula 101 for receiving the implant. The treatment of the humerus 102 includes removal of the humeral head and opening of the canal. Thereafter, a first portion of the implant comprising a stem and humeral head are attached to the humerus 102.

Figure 13:
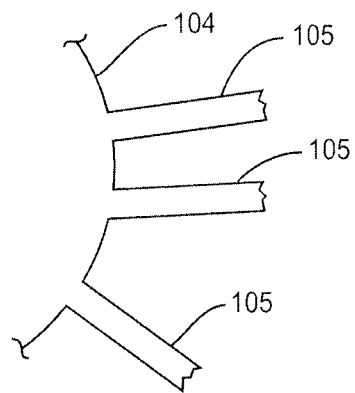
FIG. 13 is a schematic side view of openings formed in a scapula at a glenoid cavity.

Treatment of the scapula 101 includes reshaping of the glenoid cavity 104. Further, one or more openings 105 are formed in the scapula 101 at the glenoid cavity 104 as illustrated in FIG. 13. In the embodiment of FIG. 13, three openings 105 are formed at the glenoid cavity 104, although other embodiments may include more or fewer openings 105.

Figure 14:
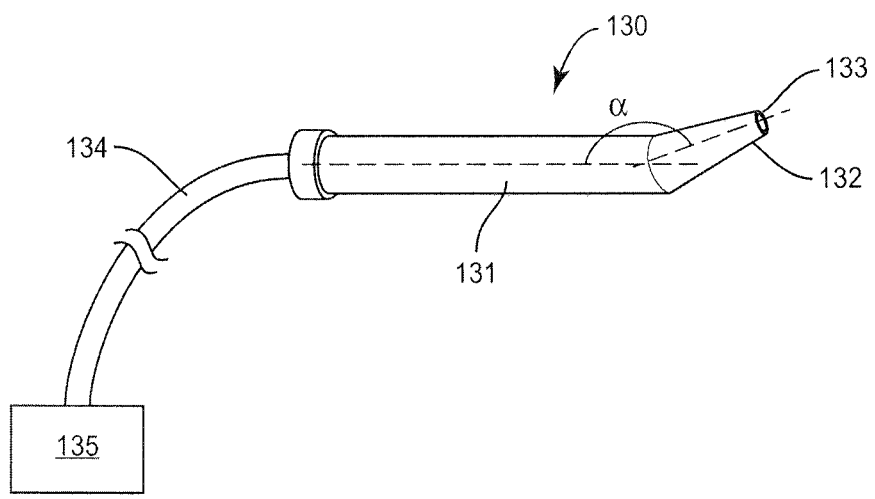
FIG. 14 is a side view of a weepstick with a conduit and a suction device.

A weepstick 130 may be inserted into one or more of the openings 105 to remove any loose materials and/or fluids. As illustrated in FIG. 14, the weepstick 130 includes an elongated hollow body with a first section 131 and a second section 132. The lengths of each of the sections 131, 132 may vary depending upon the use. In one embodiment, the first section 131 includes a length of about seven inches. The first and second sections 131, 132 may each be substantially straight, and aligned at an angle α that may range from between about 130 degrees to about 160 degrees. In one specific embodiment, the angle is about 160 degrees.

The first section 131 may include a substantially constant width, or may include a variable width. Likewise, the second section 132 may include a constant or variable width. In one embodiment, the second section 132 includes a tapered width that narrows towards the distal end 133. The end of the second section 132 adjacent to the first section 131 may be larger than the opening 105 to allow the weepstick 130 to seat against the outer edges of the opening 105 and provide a seal to improve the suction.

The weepstick 130 is hollow with the inlet 133 at the distal end configured to receive the materials in the openings 105. A suction device 135 is attached to the weepstick 130 either directly or through a conduit 134.

In one embodiment, a portion or entirety of the second section 132 includes a rubberized coating.

In one embodiment, the weepstick 130 has substantially the same shape and configuration as the nozzle 30 but does not include a flange 37.

In use, the weepstick 130 is inserted into the patient with the second section 132 being sized to fit within the openings 105. The angled configuration of the weepstick 130 facilitates insertion of the second section 132 into the openings 105. Once inserted, the suction through the weepstick 130 removes any materials from the openings 105. The removed materials enter the weepstick 130 through the inlet 133, are moved along the length of the weepstick 150, and into a reservoir placed either along the conduit 134 or at the suction device 135.

Figure 15:
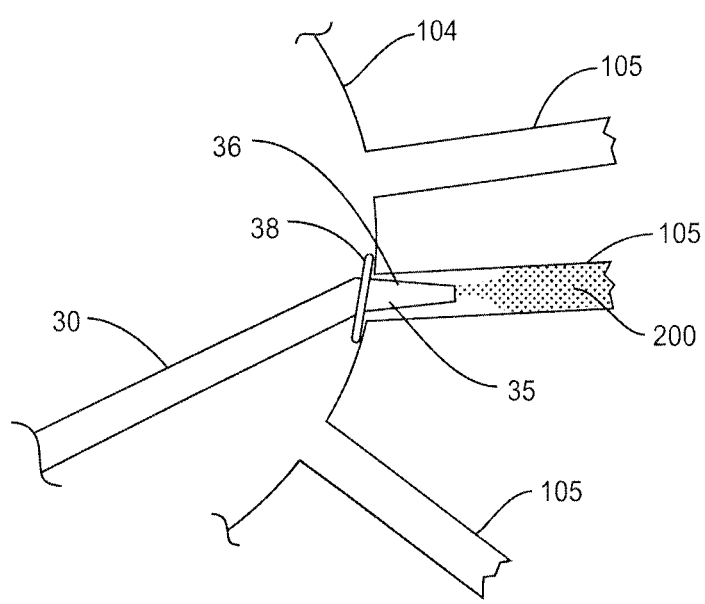
FIG. 15 is a schematic side view of a nozzle inserted in an opening in a scapula.

Once the materials have been removed from the openings 105, cement 200 is inserted into each of the openings 104. The device 10 is used to insert the cement 200 into each of the openings 104. This includes inserting the second end 32 of the nozzle 30 into each opening 105. As illustrated in FIG. 15, the nozzle 30 is inserted a distance such that the bumper 38 abuts against the surface of the glenoid cavity 104. Once positioned, the plunger 40 is depressed thereby forcing the cement 200 from the body 20, through the nozzle 30, and into the opening 105. The bumper 105 provides for the surgeon to determine the extent of insertion of the nozzle 30 into the opening 105. Further, the bumper 38 may also prevent the cement 200 from escaping from the opening 105. In embodiments with a flange 37, the flange 37 operates in a similar manner remaining on the exterior of the opening 105.

Once the cement is inserted, a glenoid component is attached to the scapula 101. In one embodiment, screws are inserted into the openings 105 to attach the component. As illustrated in FIG. 15, the angled second section 35 of the nozzle 30 facilitates placement into the openings 105.

In one specific embodiment, the removal of materials and the adding of cement to the openings 105 are performed in a particular manner. After the openings 105 are formed, the weepstick 130 is inserted into at least the outer openings 105 to remove any materials. Once complete, cement is inserted by the device 10 into the outer openings 105. Once the cement is in the outer openings 105, the weepstick 130 is inserted into a central opening that does not include cement. The suction applied to the glenoid cavity 104 through the weepstick 130 removes any materials from the openings 105 and also causes the cement in the outer openings 105 to be drawn into the cancellous bone of the scapula 101. Once this is complete, the weepstick 130 is removed from the opening 105 and the device 10 is inserted to add cement. A glenoid component is then attached to the scapula 101. In one embodiment, screws are inserted into the openings 105 to attach the component.

In one specific embodiment, a total of three openings 105 are formed at the glenoid cavity 104 as illustrated in FIG. 15. Cement is placed in the outer two openings 105, and then the weepstick 130 is inserted into the middle opening 105 to draw the cement into the cancellous bone. Other embodiments may include a variety of openings 105 and placement of the weepstick 130 after cement has been added.

Figure 16:
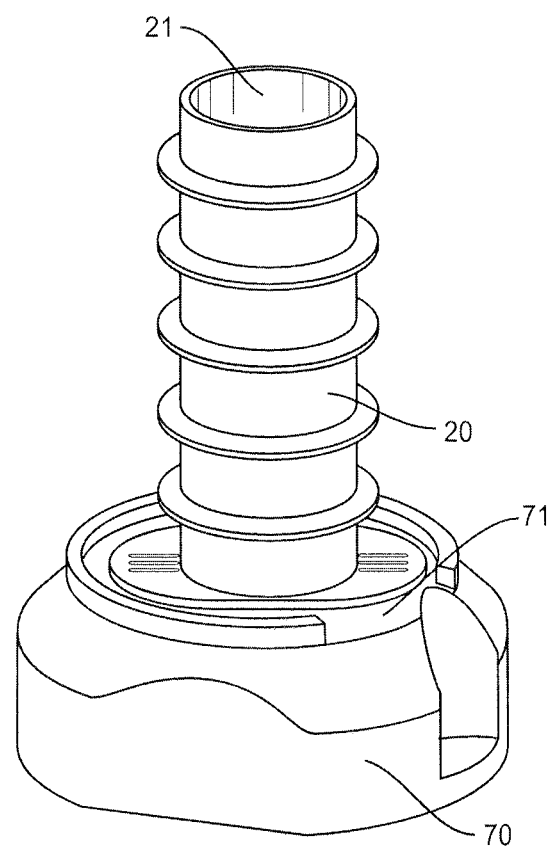
FIG. 16 is a perspective view of a body extending outward from a base.
Figure 17:
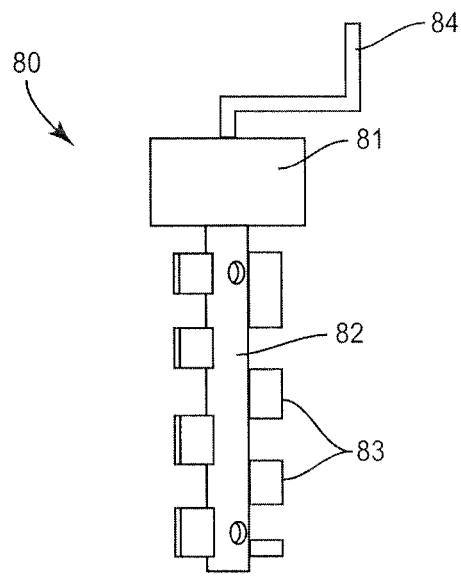
FIG. 17 is a side view of a mixing member.

A mixing system may also be included with the device 10. As illustrated in FIGS. 16 and 17, the system includes a base 70 to mount the body 20 in an upright position with the threaded end facing upwards. The body 20 includes the second end removed (as illustrated in FIG. 4) with the receptacle 21 being accessible. In one embodiment, the base 70 is configured to also receive the plunger 40. In another embodiment, the opposing end of the receptacle 21 is covered to prevent escape of the cement.

With the body 20 being in the position as illustrated in FIG. 14, cement is inserted into the receptacle 21. Thereafter, a mixing member 80 as illustrated in FIG. 17 is attached to the body 20. The mixing member 80 includes a mount 81 configured to attach to the body 20. In one embodiment, the mount 81 includes a cap-like member with a threaded interior to engage with corresponding threads on the body 20. The member 80 also includes a shaft 82 and one or more paddles 83. A handle 84 is attached to the shaft 82 and extends outward from an opposing side of the mount 81.

In use, the mount 81 is threaded onto the body 20 with the shaft 82 and paddles 83 positioned in the cement in the receptacle 21. Once attached, the handle 84 is rotated thus rotating the shaft 82 and paddles 83 and mixing the cement. Once complete, the member 80 is removed from the body 20. The second end 23 of the body (see FIG. 4) is threaded onto the body and the device 10 may be used to deliver the cement.

The various implants and insertion tools may be used during surgical procedures on living patients. These may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of inserting bone cement into a scapula a patient comprising:
    forming first and second openings in the scapula of the patient at a face of the glenoid cavity;
    inserting a first section of a nozzle including a leading tip into the first opening;
    positioning a second section of the nozzle on the exterior of the first opening, each of the first and second sections being straight and being aligned relative to one another at an obtuse angle;
    positioning a flexible bumper against the face of the glenoid cavity with the flexible bumper positioned along the first section of the nozzle and extending radially outward from the first section of the nozzle;
    moving the bone cement through an interior of the nozzle and through the leading tip and into the first opening in the glenoid cavity;
    filling the first opening with the bone cement and preventing the bone cement from escaping from the first opening by the flexible bumper that is positioned against the face of the glenoid cavity;
    inserting a tip of a suction device into the second opening in the glenoid cavity and applying suction through the suction device to the second opening and drawing the bone cement into the cancellous bone of the scapula from the first opening in the glenoid cavity; and after applying the suction, removing the tip of the suction device from the second opening and inserting the first section of the nozzle into the second opening and filling the second opening with the bone cement.

2. The method of claim 1, further comprising the first section of the nozzle having a tapered shape that decreases in size towards the tip and the second section includes a non-tapered shape.

3. The method of claim 1, further comprising abutting a first side of the bumper against the face of the glenoid cavity and abutting an opposing second side against a radial flange on the nozzle.

4. The method of claim 1, further comprising flexing the bumper against the face of the glenoid cavity with the bumper being constructed from a foam material.

5. The method of claim 1, further comprising moving a plunger through a body and forcing the bone cement from the body, through the nozzle, and through the leading tip.

6. The method of claim 1, further comprising a hollow body attached to a proximal end of the nozzle, with the bone cement being mixed in the body prior to being expelled through the leading tip.

7. The method of claim 1, further comprising overlapping a portion of the bumper across the scapula adjacent to the glenoid cavity.

8. The method of claim 1, further comprising attaching a component to the scapula at the openings.

9. The method of claim 1, further comprising inserting screws in the openings and attaching a component to the scapula.

10. A method of inserting bone cement into a scapula a patient comprising:

forming openings in the scapula of the patient at a face of the glenoid cavity;

inserting a nozzle into a first one of the openings and abutting a flexible bumper against the face of the glenoid cavity;

moving the bone cement through the nozzle and into the first opening and preventing the bone cement from escaping from the first opening by the flexible bumper;

inserting the nozzle into a second one of the openings and abutting the flexible bumper against the face of the glenoid cavity, the second opening being spaced away from the first opening;

moving the bone cement through the nozzle and into the second opening and preventing the bone cement from escaping from the second opening by the flexible bumper;

applying a tip of a suction device into a third one of the openings and applying suction through the suction device and drawing the bone cement into the cancellous bone of the scapula from each of the first and second openings, the third opening being located in proximity to each of the first and second openings; and after applying the suction, removing the tip of the suction device from the third opening, inserting the nozzle into the third opening and abutting the flexible bumper against the face of the glenoid cavity and moving the bone cement through the nozzle and filling the third opening with the bone cement.

11. The method of claim 10, further comprising filling the first opening with the bone cement and preventing the bone cement from escaping from the first opening by the flexible bumper that is positioned against the face of the glenoid cavity.

12. The method of claim 10, further comprising attaching a component to the scapula at the openings.

13. The method of claim 10, further comprising inserting screws in the openings and attaching a component to the scapula.

* * * * *